United States Patent [19]
Cheney, III

[11] Patent Number: 5,143,048
[45] Date of Patent: Sep. 1, 1992

[54] DISPOSABLE INFANT HEEL WARMER

[75] Inventor: Henry H. Cheney, III, Campton, N.H.

[73] Assignee: Consolidated Products and Services, Inc., Quincy, Mass.

[21] Appl. No.: 763,967

[22] Filed: Sep. 23, 1991

[51] Int. Cl.$^5$ .............................................. F24J 1/00
[52] U.S. Cl. ...................................... 126/263; 126/204
[58] Field of Search ................ 126/204, 206, 263; 62/4; 422/245; 128/399–403; 362/34; 252/70

[56] References Cited

U.S. PATENT DOCUMENTS

| | | | |
|---|---|---|---|
| 2,541,736 | 2/1951 | Alexander | 126/263 |
| 4,292,517 | 10/1981 | Guex et al. | 126/263 |
| 4,332,690 | 6/1982 | Kimura et al. | 252/70 |
| 4,361,491 | 11/1982 | Truelock | 126/263 |
| 4,451,383 | 5/1984 | Arrhenius | 126/263 |
| 4,823,769 | 4/1989 | Semaan | 126/263 |
| 4,860,729 | 8/1989 | Benson | 126/263 |
| 4,865,012 | 9/1989 | Kelley | 126/204 |

Primary Examiner—James C. Yeung
Attorney, Agent, or Firm—John P. McGonagle

[57] ABSTRACT

A heat pack comprised of a supercooled aqueous solution of sodium acetate and hydroxyethyl cellulose together with a plastic or glass disk or ampule containing sodium acetate crystals in a sealed, flexible container. Activation or crystallization of the sodium acetate portion of the solution is produced by breaking the disk or ampule and exposing the solution to the sodium acetate crystals.

6 Claims, 3 Drawing Sheets

DISPOSABLE INFANT HEEL WARMER

BACKGROUND OF THE INVENTION

This invention relates to disposable chemical thermal packs, and more particularly to triggers for activating such packs.

Most hospitals require that blood samples be taken from new born infants during the first days after birth. Since one of the biggest body masses of a new born is his or her heel, blood for tests is generally drawn from the heel area. The problem with the heel as a source of blood is that a new born's blood circulation is poor. If blood circulation in the heel area is not increased before testing, drawing blood for testing may have an adverse affect on the infant and cause complications.

It is well known that heat causes blood flow to increase at the site where the heat is applied. Heat applied to the new born's heel area before blood is drawn for testing will increase blood flow into the heel area and prevent complications from the test.

Heat packs have long been used in various forms in the medical and sports fields. They are particularly useful for warming the heels of new born infants before blood is drawn for various tests. Current heat packs utilize supercoolable aqueous salt solutions wherein the temperatures as well as the duration of the heat given off can be controlled. Various salt solutions such as sodium acetate and calcium nitrate tetrahydrate are examples of such solutions.

Heat packs used as heel warmers today are of the reusable type. They feature a supercoolable aqueous solution together with a metallic activator device. Metallic activators have well documented problems associates with their use, but are still used to ensure reusability of the pack.

SUMMARY OF THE INVENTION

In view of the foregoing disadvantages inherent in the known types of devices now presently used in the prior art, the present invention provides a disposable heat pack which eliminates the need for a metallic trigger. As such, the general purpose of the present invention, which will be described subsequently in greater detail, is to provide a new and improved infant heel warmer which triggers the heat pack by exposing a supercooled aqueous solution of sodium acetate and hydroxyethyl cellulose to sodium acetate crystals.

To attain this a supercoolable aqueous sodium acetate and hydroxyethyl cellulose solution together with a plastic or glass disk or ampule containing sodium acetate crystals is enclosed in a sealed, flexible container. Activation or crystallization of the sodium acetate solution is produced by breaking the disk or ampule and exposing the solution to the sodium acetate crystals.

Activation of the pack will cause heat to be evolved. The amount of heat and duration is easily controlled. After use, the heat pack is simply disposed of, thereby greatly reducing cost and the problems inherent with metallic triggering devices.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF THE INVENTION

Figure 1:
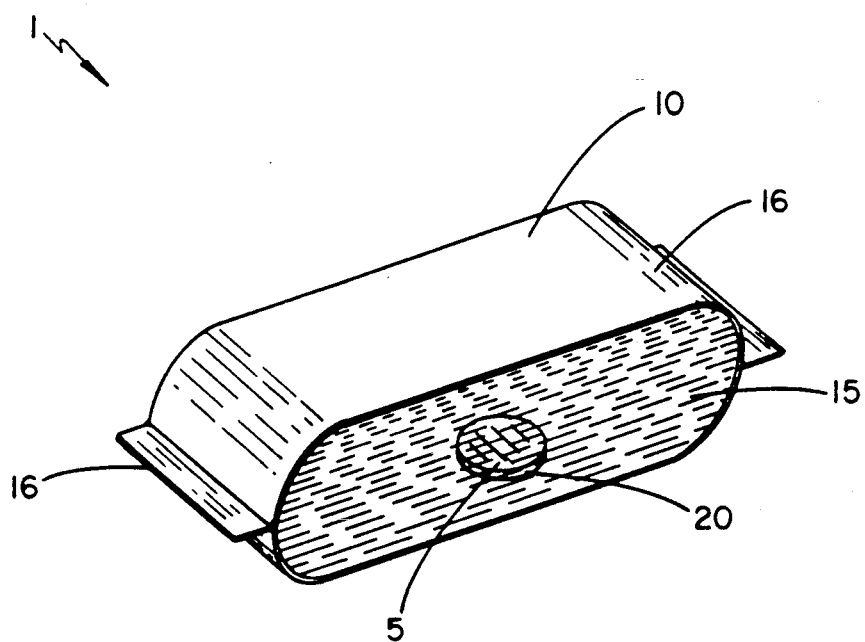
FIG. 1 is perspective, sectional view of the herein described heel warmer.
Figure 2A:
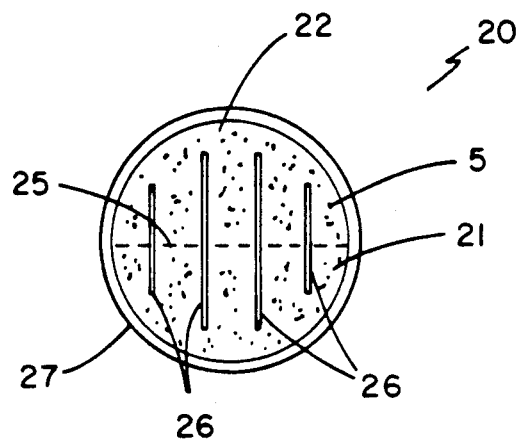
FIGS. 2A and 2B are a plan view and a side edge view, respectively, of one embodiment of the container holding the activator crystals which may be used in the heel warmer of FIG. 1.
Figure 2B:
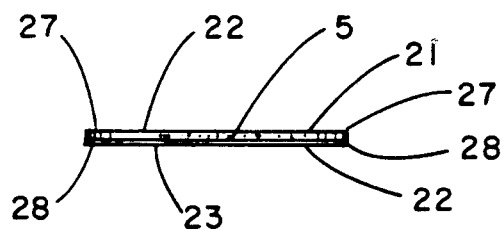
Figure 3:
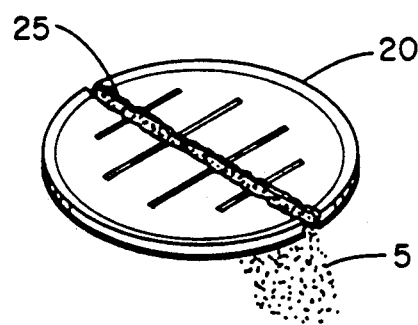
FIG. 3 is a perspective view of the container and crystals illustrating its use.

Referring to the drawings in detail, and specifically FIGS. 1-3, wherein like elements are indicated by like numerals, there is shown an embodiment of the invention 1 incorporating a flexible container 10, an aqueous sodium acetate and hydroxyethyl cellulose solution 15, and a nonmetallic disk 20 containing sodium acetate crystal granules 5. The container 10 is made from a flexible material which is not affected by the solution 15. The material forming the container 10 is preferably clear so that the disk 20 can be easily seen. Initially the container 10 has an open end or side for introduction of the solution 15 and disk 20, whereas the other sides or edges 16 may be heat sealed. After addition of the solution 15 and disk 20, the container open end or side is sealed to make the heat pack fluid-tight. The size and shape of the heat pack 1 will vary according to its use. The main use of the hydroxyethyl cellulose in the solution 15 is as a thickening agent, a version of which is sold under the Union Carbide trade name CELLOSIZE.

The disk container 20 is comprised of two plates 21 and 22 made of a brittle acrylic or styrene plastic. Although plastic is the preferred material, a brittle glass could also be effectively used. Granular sodium acetate crystals 5 are placed between the plates 21 and 22. The plates 21, 22 are then sonically welded together so that their perimeters 27, 28 are fused together. This provides a hermetic seal which is water impermeable. The injection molding process of making the plates 21 and 22 out of a plastic results in a "Knit Line" 25 being formed across the faces 22 and 23 of each plate 21 and 22, respectively. When the disk 20 is bent, either or both of the plates 21, 22 will break along a Knit Line 25 thereby releasing one or more crystals 5 from the container 20 When the sodium acetate portion of the liquid solution 15 and crystals 5 come into contact, the sodium acetate in the solution 15 will crystalize, thereby generating heat. The solution mixture 15 is designed to generate a heat of 105 degrees ±1 degree for five minutes upon crystalization. Score lines 26 may be added to the faces 23, 24 of the plates 21, 22 to enhance breakability. In two hundred test cases, breaking of the plastic disk 20 and releasing the crystals 5 contained therein into the solution 15 caused heat pack 1 activation every time.

Figure 4:
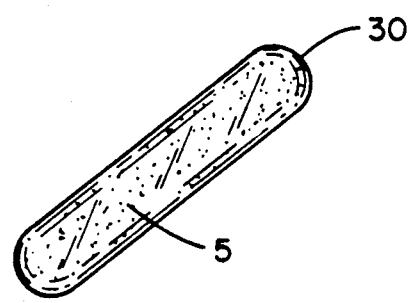
FIG. 4 is a perspective view of another embodiment of the herein-described container holding activator crystals.

FIG. 4 illustrates an alternative embodiment to the plastic disk container 20. In this embodiment a brittle glass ampule 30 containing sodium acetate crystals 5 hermetically sealed therein and impervious to liquid is used. Due to its longitudinal shape the ampule 30 is easily snapped thereby releasing the crystals 5 into the solution 15. To prevent broken glass from cutting through the flexible container 10, a wrapping material, such as paper, may be used around the ampule 30. Several holes would be drilled through the wrapper to ensure that the sodium acetate crystals come into contact with the solution 15.

It is understood that the above-described embodiment is merely illustrative of the application. Other embodiments may be readily devised by those skilled in the art which will embody the principles of the invention and fall within the spirit and scope thereof.

I claim:

1. A disposable heat pack for warming the heel of an infant comprising:
   a flexible container;
   a supercooled aqueous sodium acetate solution carried within said flexible container; and
   a nonmetallic, hermetically sealed container, comprised of two plates having perimeters fused together, containing sodium acetate crystal granules, said plates being made of a brittle plastic and each containing a knit line, said hermetically sealed container being confined within said flexible container in contact with said aqueous solution.

2. A heat pack according to claim 1, wherein:
   each plate is scored to enhance breakability.

3. A heat pack according to claim 2, wherein:
   said supercooled solution contains a thickening agent.

4. A heat pack according to claim 3, wherein:
   said thickening agent is hydroxyethyl cellulose.

5. In a disposable heat pack for warming the heel of an infant, said heat pack being comprised of a flexible container having a supercooled aqueous sodium acetate solution carried within said flexible container, a trigger to initiate crystallization of said aqueous solution, said trigger being confined within said container in contact with said aqueous solution, wherein during crystallization the crystallized solution gives off heat from an exothermic reaction and the heat pack may be used for applying heat to the body where desired, said trigger comprising:
   a nonmetallic, hermetically sealed container containing sodium acetate crystal granules, said container being comprised of two plates having perimeters fused together, each of said plates being made of a brittle plastic and having a knit line.

6. A trigger in accordance with claim 5, wherein:
   each plate is scored to enhance breakability.

* * * * *